(12) United States Patent
Zhang

(10) Patent No.: US 7,306,812 B2
(45) Date of Patent: Dec. 11, 2007

(54) DISSOLVABLE BACKING LAYER FOR USE WITH A TRANSMUCOSAL DELIVERY DEVICE

(75) Inventor: Hao Zhang, Foster City, CA (US)

(73) Assignee: Cephalon, Inc., Frazer, PA (US)

( * ) Notice: Subject to any disclaimer, the term of this patent is extended or adjusted under 35 U.S.C. 154(b) by 672 days.

(21) Appl. No.: 10/841,893

(22) Filed: May 7, 2004

(65) Prior Publication Data

US 2004/0224008 A1 Nov. 11, 2004

Related U.S. Application Data

(60) Provisional application No. 60/469,507, filed on May 9, 2003.

(51) Int. Cl.
A61F 13/00 (2006.01)
A61F 2/00 (2006.01)

(52) U.S. Cl. ...................... 424/434; 424/426

(58) Field of Classification Search ............... 424/426, 424/427, 428, 430, 434, 435, 436, 448, 449
See application file for complete search history.

(56) References Cited

U.S. PATENT DOCUMENTS

| | | | |
|---|---|---|---|
| 4,226,848 A | 10/1980 | Nagai et al. |
| 4,250,163 A | 2/1981 | Nagai et al. |
| 4,292,299 A | 9/1981 | Suzuki et al. |
| 4,307,075 A | 12/1981 | Martin |
| 4,517,173 A | 5/1985 | Kizawa et al. |
| 4,572,832 A | 2/1986 | Kigasawa et al. |
| 4,573,996 A | 3/1986 | Kwiatek et al. |
| 4,615,697 A | 10/1986 | Robinson |
| 4,704,119 A | 11/1987 | Shaw et al. |
| 4,713,243 A | 12/1987 | Schiraldi et al. |
| 4,740,365 A | 4/1988 | Yukimatsu et al. |
| 4,755,386 A | 7/1988 | Hsiao et al. |
| 4,764,378 A | 8/1988 | Keith et al. |
| 4,765,983 A | 8/1988 | Takayanagi et al. |
| 4,788,209 A | 11/1988 | Baumann et al. |
| 4,866,046 A | 9/1989 | Amer |
| 4,876,092 A | 10/1989 | Mizobuchi et al. |
| 4,900,552 A | 2/1990 | Sanvordeker et al. |
| 4,900,554 A | 2/1990 | Yanagibashi et al. |
| 5,021,053 A | 6/1991 | Barclay et al. |
| 5,053,032 A | 10/1991 | Barclay et al. |
| 5,073,374 A | 12/1991 | McCarty |
| 5,110,605 A | 5/1992 | Acharya |

(Continued)

FOREIGN PATENT DOCUMENTS

EP 0873750 10/1998

(Continued)

*Primary Examiner*—Sharon E. Kennedy (57) ABSTRACT

A dissolvable backing layer for use with transmucosal drug delivery devices includes a dissolvable hydrophilic region and a non-hydrophilic region that inhibits or slows migration of water, drugs, other active agents, or other molecules through the backing layer. The non-hydrophilic region can be a disperse phase of gaseous voids, droplets of a hydrophobic liquid, solid particles of a hydrophobic material, or water insoluble particles that are not necessarily hydrophobic. In the alternative, the non-hydrophilic region may comprise a continuous layer or component that is readily dispersible upon dissolving of the hydrophilic region. The backing layers may be used within any transmucosal delivery device used to delivery drugs or other active agents across a mucosal surface.

60 Claims, 4 Drawing Sheets

U.S. PATENT DOCUMENTS

| | | |
|---|---|---|
| 5,112,616 A | 5/1992 | McCarty |
| 5,113,860 A | 5/1992 | McQuinn |
| 5,147,648 A | 9/1992 | Bannert |
| 5,147,654 A | 9/1992 | Place et al. |
| 5,204,108 A | 4/1993 | Illum |
| 5,248,310 A | 9/1993 | Barclay et al. |
| 5,288,498 A | 2/1994 | Stanley et al. |
| 5,298,256 A | 3/1994 | Flockhart et al. |
| 5,326,685 A | 7/1994 | Gaglio et al. |
| 5,346,701 A | 9/1994 | Heiber et al. |
| 5,482,706 A | 1/1996 | Igari et al. |
| 5,512,293 A | 4/1996 | Landrau et al. |
| 5,512,299 A | 4/1996 | Place et al. |
| 5,516,523 A | 5/1996 | Heiber et al. |
| 5,529,782 A | 6/1996 | Staab |
| 5,573,776 A | 11/1996 | Harrison et al. |
| 5,578,315 A | 11/1996 | Chien et al. |
| 5,599,554 A | 2/1997 | Majeti |
| 5,603,947 A | 2/1997 | Wong et al. |
| 5,624,677 A | 4/1997 | El-Rashidy et al. |
| 5,639,469 A | 6/1997 | Benes et al. |
| 5,650,192 A | 7/1997 | Britton et al. |
| 5,656,284 A | 8/1997 | Balkin |
| 5,679,373 A | 10/1997 | Wick et al. |
| 5,679,714 A | 10/1997 | Weg |
| 5,700,478 A | 12/1997 | Biegajski et al. |
| 5,725,853 A | 3/1998 | Dennis et al. |
| 5,750,136 A | 5/1998 | Scholz et al. |
| 5,763,476 A | 6/1998 | Delbressine et al. |
| 5,766,620 A | 6/1998 | Heiber et al. |
| 5,776,493 A | 7/1998 | Barclay et al. |
| 5,783,207 A | 7/1998 | Stanley et al. |
| 5,800,832 A | 9/1998 | Tapolsky et al. |
| 5,827,525 A | 10/1998 | Liao et al. |
| 5,849,322 A | 12/1998 | Ebert et al. |
| 5,855,908 A | 1/1999 | Stanley et al. |
| 5,863,555 A | 1/1999 | Heiber et al. |
| 5,869,096 A | 2/1999 | Barclay et al. |
| 5,888,534 A | 3/1999 | El-Rashidy et al. |
| 5,891,458 A | 4/1999 | Britton et al. |
| 5,900,247 A | 5/1999 | Rault et al. |
| 5,908,637 A | 6/1999 | Benes et al. |
| 5,981,552 A | 11/1999 | Alam |
| 5,989,582 A | 11/1999 | Weg |
| 6,087,362 A | 7/2000 | El-Rashidy |
| 6,117,446 A | 9/2000 | Place |
| 6,121,276 A | 9/2000 | El-Rashidy et al. |
| 6,146,655 A | 11/2000 | Ruben |
| 6,147,102 A | 11/2000 | Borgman |
| 6,159,498 A | 12/2000 | Tapolsky et al. |
| 6,177,096 B1 | 1/2001 | Zerbe et al. |
| 6,180,682 B1 | 1/2001 | Place |
| 6,183,775 B1 | 2/2001 | Ventouras |
| 6,193,992 B1 | 2/2001 | El-Rashidy et al. |
| 6,197,331 B1 | 3/2001 | Lerner et al. |
| 6,200,593 B1 | 3/2001 | Place |
| 6,200,604 B1 | 3/2001 | Pather et al. |
| 6,210,699 B1 | 4/2001 | Acharya et al. |
| 6,221,379 B1 | 4/2001 | Place |
| 6,228,864 B1 | 5/2001 | Smith et al. |
| 6,241,529 B1 | 6/2001 | Place |
| 6,242,004 B1 | 6/2001 | Rault |
| 6,248,789 B1 | 6/2001 | Weg |
| 6,255,502 B1 | 7/2001 | Penkler et al. |
| 6,264,974 B1 | 7/2001 | Madhat |
| 6,264,981 B1 | 7/2001 | Zhang et al. |
| 6,284,262 B1 | 9/2001 | Place |
| 6,284,263 B1 | 9/2001 | Place |
| 6,284,264 B1 | 9/2001 | Zerbe et al. |
| 6,294,550 B1 | 9/2001 | Place et al. |
| 6,306,437 B1 | 10/2001 | El-Rashidy et al. |
| 6,306,841 B1 | 10/2001 | Place et al. |
| 6,319,510 B1 | 11/2001 | Yates |
| 6,375,963 B1 | 4/2002 | Repka et al. |
| 2001/0006677 A1 | 7/2001 | McGinity et al. |
| 2002/0068151 A1 | 6/2002 | Kim et al. |
| 2004/0028732 A1 | 2/2004 | Falkenhausen et al. |

FOREIGN PATENT DOCUMENTS

| | | |
|---|---|---|
| WO | WO 99/55312 | 11/1999 |
| WO | WO 00/72827 | 12/2000 |
| WO | WO 02/02085 | 1/2002 |
| WO | WO 03/015748 | 2/2003 |

DISSOLVABLE BACKING LAYER FOR USE WITH A TRANSMUCOSAL DELIVERY DEVICE

This application claims benefit of U.S. Provisional Application Ser. No. 60/469,507 filed May 9, 2003.

BACKGROUND OF THE INVENTION

1. Field of the Invention

The present invention is in the field of transmucosal drug delivery devices, particularly in the field of transmucosal patches for use in isolating and maintaining a drug or other active ingredient against a mucosal surface in order to promote diffusion of the drug or other active agent therethrough, and more particularly in the field of backing layers for transmucosal patches.

2. Relevant Technology

Transmucosal drug delivery is an alternative method of systemic drug delivery. It offers several advantages over both injectable and enteral delivery. Drugs absorbed via the mucous membrane (e.g., oral, anal or vaginal mucosa) avoid the low pH gastric fluid and proteases, as well as first-pass metabolism in the liver. The onset of action is faster than oral administration. Unlike injections, transmucosal delivery is non-invasive and not painful. Moreover, a patient can administer the medicine without help from a medical professional.

There is considerable interest in developing new dosage forms that can deliver drugs and other active agents across the mucosa of humans and mammals. In general, oral and other transmucosal dosage forms can be classified in one of three categories: (1) solid forms, (2) gum, and (3) patches. Examples of common solid dosage forms include lozenges, lozenges having a handle (e.g., lollipops), buccal tablets, and sublingual tablets. As the solid matrix dissolves in the oral cavity it releases the drug, which is absorbed by the oral mucosa. This type of dosage form is referred to as an "open system" because saliva can flow freely to and from the dosage form to dissolve the formulation. Drug concentration is generally controlled by how fast the matrix is dissolved, which is controlled by how fast the patient sucks the unit.

Gum, like lozenges and tablets, is an open system. When this dosage form is chewed the drug is released from gum into the oral cavity where it can be absorbed by oral mucosa. Drug release from gum is controlled by the make up of the delivery device, as well as how fast the gum is chewed. In general, gum dosage forms last longer than lozenges or tablets.

The term "buccal patch" typically refers to a flexible film that adheres to the oral mucosa and delivers a drug over a period of time. The buccal patch dosage form can be further divided into three types or subcategories: (1) dissolvable matrix patches, (2) patches having a non-dissolvable backing, and (3) patches with a dissolvable backing.

For examples known in the art of buccal patch technology see U.S. Pat. No. 3,598,122; U.S. Pat. No. 3,972,995; U.S. Pat. No. 4,517,173; U.S. Pat. No. 4,573,996; U.S. Pat. No. 4,572,832; U.S. Pat. No. 4,704,119; U.S. Pat. No. 4,713,243; U.S. Pat. No. 4,715,369; U.S. Pat. No. 4,740,365; U.S. Pat. No. 4,855,142; U.S. Pat. No. 4,876,092; U.S. Pat. No. 4,900,552; U.S. Pat. No. 4,900,554; U.S. Pat. No. 5,137,729; U.S. Pat. No. 5,298,256; U.S. Pat. No. 5,346,701; U.S. Pat. No. 5,516,523; U.S. Pat. No. 5,578,315; U.S. Pat. No. 5,599,554; U.S. Pat. No. 5,639,469; U.S. Pat. No. 5,766,620; U.S. Pat. No. 5,800,832; U.S. Pat. No. 5,863,555; U.S. Pat. No. 5,900,247; U.S. Pat. No. 6,159,498; U.S. Pat. No. 6,210,699; and U.S. Pat. No. 6,319,510.

Dissolvable matrix patches work similar to gum, lozenge and tablet dosage forms. The dissolving matrix releases the drug into the oral cavity for absorption by oral mucosa. They usually last longer than lozenges or tablets. Unlike gum, dissolvable matrix patches release the drug passively rather than actively. One limitation of all these systems is that the drug concentration in the mouth is not well controlled. In order to control the drug concentration over the period of drug delivery, buccal patches with backings were developed. Controlling drug concentration is particularly important when mucosally delivering drugs that require the help of permeation enhancers. Permeation enhancers are chemicals that can temporarily compromise the integrity of the oral mucosa so that drug delivery can be enhanced. The concentration of enhancers needs to be carefully controlled. If the concentration is too high, the enhancer can cause mucosal irritation or damage. If too low, it may not provide the desired enhancement of drug delivery. One way to maintain control of both drug and enhancer concentration is to include a backing so that the active formulation of the buccal patch is completely isolated from the surrounding environment, especially the saliva of the oral cavity.

There are two types of backing systems in the buccal patch dosage form: dissolvable and non-dissolvable. Non-dissolvable backings are usually flexible. They are designed to stay in the oral cavity for long periods of time, e.g., up to 10-15 hours. The disadvantage is that the patch has to be removed from oral mucosa by the patient after drug administration.

Patches with dissolvable backings are designed to stay in the oral cavity for a short period of time. The backing controls the local environment inside the patch so that high efficient drug delivery can be achieved in a controlled fashion. Over time, the backing dissolves or disintegrates in the oral cavity (e.g., when exposed to saliva) in order for all or part of the delivery device to go away. Such devices eliminate the need to remove the patch after treatment has been completed.

One of the challenges of providing patches with a dissolvable and/or disintegratable backing has been the need to provide materials that are able to provide an adequate barrier, in order to control the drug and/or permeation enhancer concentration over the period of drug delivery, while still being able to dissolve and/or disintegrate over time. There is an ongoing need to develop improved backing layers for use with transmucosal delivery devices, especially oral transmucosal delivery devices, that are able to dissolve and/or disintegrate over time when exposed to moisture; and that also provide sufficient barrier properties so as to prevent, or at least partially inhibit or slow, the tendency of drugs or other active agents from diffusing through the backing layer. The present invention overcomes shortcomings of prior art devices.

SUMMARY OF THE INVENTION

The present invention relates to backing layers for use with transmucosal drug delivery devices that are able to dissolve or otherwise disintegrate over time when exposed to moisture (e.g., saliva found within the oral cavity) and which are able to prevent, or at least partially inhibit or slow, the diffusion of water, drugs, other active agents, or other molecules therethrough. As used in the specification and claims, the terms "dissolve", "dissolving" and "dissolvable" include, but are not necessarily limited to, what is meant by the terms "dissolve" and "disintegrate", "dissolving" and "disintegrating", or "dissolvable" and disintegratable", respectively. Similarly, the term "water-dissolvable" includes, but is not limited to, "water-disintegratable". For example, as used herein a dissolvable layer may separate into components when exposed to moisture and optionally pass into solution or it may pass directly into solution when exposed to moisture. The term "active agent" broadly includes any drug, hormone, vitamin, nutrient, or molecule that is intended for transmucosal delivery.

The inventive backing layers are typically used in combination with one or more layers within a transmucosal delivery device. In one aspect of the invention, the inventive backing layers are used in combination with one or more active layers in order to isolate an active agent against a mucosal surface while preventing, or at least partially inhibiting or slowing, diffusion of the active agent away from the mucosal surface and into the surrounding environment. In the case of a buccal patch, for example, the inventive backing layer prevents, inhibits or slows infusion of the active agent into the oral cavity, where it can be swallowed or expectorated.

Backing layers according to the invention include hydrophilic and non-hydrophilic regions that allow the backing layer to provide good dissolvability in moisture over a prescribed period of time, while also inhibiting or slowing the diffusion of water from the surrounding environment into the dosage form and inhibiting or slowing the diffusion of the active agent out of the dosage form and into the surrounding environment. The term "non-hydrophilic region" is defined as any region other than the "hydrophilic region". Examples of non-hydrophilic regions include a hydrophobic liquid phase (e.g., oil droplets or layers), a hydrophobic semisolid phase (e.g., hydrogenated vegetable oil droplets or layers), a hydrophobic solid phase (e.g., fatty acids, wax particles), voids (e.g., gaseous bubbles), and solids (e.g., non-dissolvable solid particles). The non-hydrophilic region may comprise one or more hydrophobic phases.

In general, the "hydrophilic region" comprises at least one hydrophilic polymer material that forms a matrix that holds the backing layer together prior to use, but which dissolves over time when exposed to moisture (e.g., saliva found within the oral cavity of a patient).

The non-hydrophilic region is included within the backing layer (e.g., within the hydrophilic region) in order to provide a barrier to the diffusion of water, drugs, or other active agents through the backing layer during the time before which the backing layer dissolves. The non-hydrophilic region can form a continuous barrier or, in the alternative, it can form a discontinuous barrier that, in effect, creates a more tortuous or circuitous route along which the drug or other active agent must travel before it is able to diffuse all the way through the backing layer.

In one embodiment, the non-hydrophilic region comprises a disperse phase within a continuous hydrophilic region (e.g., in the form of gaseous voids, oil droplets, wax particles, plastic or other solids, or insoluble inorganic particulates). An advantage of providing a non-hydrophilic region as a disperse phase is that it enhances the ability of the non-hydrophilic region to disperse upon dissolving of the hydrophilic region. In the case of a continuous non-hydrophilic region, or a non-hydrophilic region that is relatively large, it will generally be desirable for the non-hydrophilic region to comprise a material that is a gas or liquid at body temperature or that is designed to otherwise readily disperse upon dissolving of the hydrophilic region. This assists the general ability of the backing layer to readily dissolve over time when used to deliver a drug or other active agent across a mucosal layer.

The backing layers according to the invention may be used in any transmucosal delivery device known in the art. They are particularly well-suited for use with transmucosal delivery devices used to deliver a drug or other active agent under a closed environment. The backing layers according to the invention can be formulated so as to resist dissolving and provide an effective barrier layer during a prescribed period of time. In this way, the backing layers according to the invention can facilitate the manufacture of delivery devices that do not need to be peeled off and discarded in the normal manner as required with non-dissolvable buccal patches or other delivery devices known in the art.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to backing layers for use with transmucosal drug delivery devices that include hydrophilic and non-hydrophilic regions or components in order to provide the dual function of being able to dissolve when exposed to moisture over time while inhibiting or slowing the diffusion of water, drugs, other active agents, or other molecules through the backing layer. The inventive backing layers are suitable for use with any transmucosal delivery devices known in the art.

The inventive backing layers according to the invention may include a variety of components which together form hydrophilic and non-hydrophilic regions that yield a backing layer that is dissolvable when exposed to moisture and that inhibits or slows the migration of water, drugs or other molecules therethrough compared to a backing layer that does not include the non-hydrophilic region. When a given numeric value is preceded by the term "about", the effect of the term "about" is to define a range that is ±10% of the given numeric value.

Hydrophilic Region or Component.

The hydrophilic region or component generally comprises one or more hydrophilic polymers that have the property of being dissolvable and/or disintegratable in saliva. Examples of hydrophilic polymers that may be used in accordance with the invention include, but are not limited to, protein-based materials (e.g., gelatin and caseine), pectin, agarose, agar, chitosan, carrageenan, starch, cellulose and cellulose derivatives (e.g., methylcellulose, calcium carboxymethylcellulose, sodium carboxymethylcellulose, crosslinked polymer of sodium carboxymethylcellulose (e.g., croscarmellose sodium), microcrystalline cellulose, ethylcellulose, hydroxyethylcellulose, hydroxypropylcellulose, hydroxypropyl methylcellulose, hydroxypropylmethylcellulose phthalate, other cellulose ethers, cellulose acetate, and cellulose acetate phthalate), polyvinyl alcohol, polyvinylpyrrolidone (PVP), cross-linked povidone, guar gum, poloxamer, polyethylene glycol, polyethylene oxide, polyacrylic acid, sodium alginate, xanthan gum, other natural hydrogels, and hydrogels derived from natural products.

In addition to the hydrophilic polymer, solvents or plasticizers may be used, which make the backing layer more flexible. Examples of plasticizers include, but are not limted to, glycerin, propylene glycol, polyethylene glycol, polypropylene glycol, sugar alcohols, and corn syrup. The hydrophilic region may also include a surfactant or emulsifier so that the non-hydrophilic region is more stable in the hydrophilic region. The hydrophilic region may also include other components, such as flavorants, sweeteners, coloring agents, antiseptic agents, preservatives, and other ingredients so that the patch is more stable and promotes better patient compliance.

In one embodiment, the hydrophilic region will comprise a continuous phase that substantially or entirely surrounds or encompasses the non-hydrophilic region. Nevertheless, it is certainly within the scope of the invention to provide a non-hydrophilic region comprising two or more distinct subregions, layers or components. The time in which the hydrophilic region or component will dissolve when exposed to moisture (e.g., saliva) depends on a number of factors. These include the identity and concentrations of the various components within the hydrophilic region, the components within the non-hydrophilic region discussed more fully below, as well as their size, the thickness of the overall backing layer, the amount of moisture to which the backing layer is exposed, and the existence of agitation, movement or other external forces (e.g., tongue movements) that might accelerate the dissolving of the backing layer.

In general, the concentration of the hydrophilic polymer within the hydrophilic region will be in a range of about 1% to 100% by weight of the hydrophilic region, more preferably in a range from about 5% to about 90%, and most preferably in a range from about 10% to about 80% by weight of the hydrophilic region.

The concentration of the solvent or plasticizer within the hydrophilic region will be in a range from 0% to about 80% by weight of the hydrophilic region, more preferably in a range from about 2% to about 60%, and most preferably in a range from about 5% to about 50% by weight of the hydrophilic region.

The hydrophilic region will preferably comprise from about 10% to about 95% percent by volume of the overall backing layer, more preferably from about 15% to about 90%, and most preferably from about 20% to about 85% by volume of the backing layer.

The hydrophilic region or component, as disclosed herein, may optionally contain flavorants and/or sweeteners. In addition to flavorants known to one skilled in the art, examples of flavorants include, but are not limited to, mint (for example, peppermint or spearmintl), citrus oils (for example, lemon, lime, orange, or grapefruit), fruit essences (for example, berry or cherry), grape, coconut, chocolate, clove, wintergreen, anise, vanilla, or combinations thereof. In addition to sweeteners known to one skilled in the art, examples of sweeteners include, but are not limited to, water-soluble sweeteners such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof; as well as water-soluble artificial sweeteners such as the saccharin salts, cyclamate salts, stevia, aspartame, and acesulfame potassium.

Non-Hydrophilic Region or Component.

The non-hydrophilic region may comprise either a disperse phase or a continuous phase relative to the hydrophilic region. The main purpose of the non-hydrophilic region is to inhibit or slow migration of water, drugs or other active agents or molecules through the backing layer compared to a backing layer in the absence of the non-hydrophilic region. The level of inhibition or slowing of migration need not be dramatic, but appreciably measurable. Nevertheless, in more preferred embodiments according to the invention, the inhibition or slowing of migration will be substantial (e.g., so that it takes many times longer for the targeted molecule to diffuse through the backing layer compared to a backing layer in the absence of the non-hydrophilic region).

Examples of non-hydrophilic materials that can be used as a disperse phase within the hydrophilic region include, but are not limited to, air or other gaseous bubbles or voids, droplets of one or more hydrophobic liquids, one or more types of solid hydrophobic particles, one or more types of particles that are not necessarily hydrophobic but which are not readily soluble in water, and mixtures thereof.

Examples of hydrophobic liquids that may be dispersed in droplet form throughout the hydrophilic region so as to form a disperse non-hydrophilic region include, but are not limited to, oil, vegetable oils, mineral oil, silicones, and organic polymers.

Examples of solid or semi-solid non-hydrophilic materials that may be dispersed throughout the hydrophilic region so as to form a disperse non-hydrophilic region include, but are not limited to, a wide variety of waxes, magnesium stearate, fats, fatty acids, salts of fatty acids, polymers, polymeric beads, and silicone particles.

Examples of solid particles that are not necessarily chemically hydrophobic but that are not readily water soluble and that may be dispersed throughout the hydrophilic region so as to form a disperse non-hydrophilic region include water-insoluble inorganic filler particles, examples of which include, but are not limited to, talc, sand, silica, alumina, transition metal oxides (e.g., titanium dioxide), silicates, ground geologic materials, and limestone.

As can be readily seen, virtually any material, whether in a gaseous, liquid or solid phase, can comprise the non-hydrophilic region, the only limitation being that such material provides a substantially higher barrier to water, drugs, or other active agents than the hydrophilic region. In general, it is contemplated that any GRAS ("generally regarded as safe") material can be used safely within the oral cavity in the case of a backing layer intended for use in a buccal patch or other transmucosal delivery device. Instead of a disperse phase, the non-hydrophilic region may comprise a continuous phase that effectively forms a continuous shield or barrier so as to prevent, inhibit or slow migration of the water, drugs, active agents, or other molecules through the backing layer. In one embodiment, the continuous non-hydrophilic region may comprise a continuous phase that is entirely encapsulated within the hydrophilic region, or which bifurcates the hydrophilic region into two or more subregions or layers. The non-hydrophilic region may comprise a plurality of subregions that are sufficiently large so as to effectively constitute a plurality of continuous phases rather than a disperse phase, although the notion of what constitutes a disperse phase rather than a plurality of continuous phases is a sliding scale. The continuous non-hydrophilic region or component may comprise a thin layer of a liquid or solid non-hydrophilic material that is interposed between an active layer or region containing a drug or other target molecule and at least a portion of the hydrophilic region.

In the case where the non-hydrophilic region comprises a disperse phase of relatively small voids, droplets or particles, the non-hydrophilic material may generally comprise any desired non-hydrophilic material. This is because, as the hydrophilic region disintegrates over time when exposed to moisture, the non-hydrophilic droplets or particles dispersed with the hydrophilic region will also readily disperse within the oral cavity or other place of attachment of the delivery device.

On the other hand, in the case where the non-hydrophilic region comprises one or more continuous regions of substantial size, it may be preferable for the material used to form the non-hydrophilic region to comprise a material that is substantially liquid or otherwise easily broken up and dispersed, at least at body temperature. Where the material comprising the non-hydrophilic region is a liquid at room temperature, it will generally readily disperse upon disintegration of the hydrophilic region. It is also within the scope of the invention to select a material that may be a solid or semi-solid at room temperature but which softens sufficiently when raised to body temperature so as to become more easily dispersible upon disintegration of the hydrophilic region.

The nonhydrophilic region will preferably comprise from about 5% to about 90% by volume of the overall backing layer, more preferably from about 10% to about 85%, and most preferably from about 15% to about 80% by volume of the backing layer.

As discussed above, the thickness of the backing layer generally correlates with the time it takes for the backing layer to become substantially disintegrated when exposed to moisture (e.g., saliva). In general, the backing layer, as a finished product after drying, will preferably have a thickness in a range from about 0.1 mm to about 5 mm, more preferably in a range from about 0.2 mm to about 3.5 mm, and most preferably in a range from about 0.3 mm to about 2 mm.

The backing layer can be formulated and sized so as to yield a backing layer that becomes dissolved within the oral cavity when exposed to saliva within a prescribed time period or range (or when exposed to moisture in some other region of the body). For example, the backing layer according to the invention may have a formulation and thickness in order for the backing layer to become dissolved within the oral cavity when exposed to saliva within a time period and a range from about 1 minute to about 2 hours, more preferably in a range from about 10 minutes to about 1 hour.

As discussed above, it is only necessary for the non-hydrophilic region to inhibit or slow migration of water, drugs, other active agents, or other molecules through the backing layer by some measurable amount compared to a backing layer in the absence of the non-hydrophilic region. In general, backing layers according to the invention will preferably decrease the permeability coefficient of water, drug, other active agents, or at least one other molecule by at least about 25%, more preferably by at least about 50%, and most preferably by at least about 75% compared to a backing layer in the absence of the non-hydrophilic region.

Exemplary Backing Layers and Delivery Devices

Reference is now made to the drawings, which illustrate a number of exemplary backing layers within the scope of the invention, as well as transmucosal delivery devices that include an exemplary backing layer according to the invention.

Figure 1:
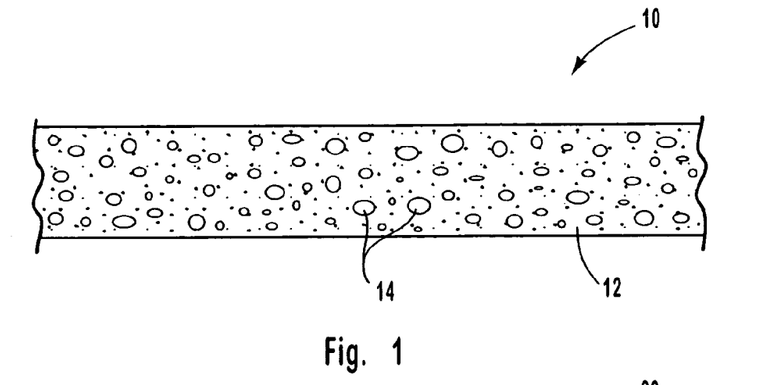
FIG. 1 is a cross-section view illustrating an exemplary backing layer according to the invention that includes a continuous hydrophilic region or component and a disperse non-hydrophilic region or component comprising gaseous voids.

FIG. 1 depicts a backing layer 10 that includes a hydrophilic region 12 and a plurality of gaseous voids 14 dispersed therein as a disperse non-hydrophilic region. Due to the initially solid nature of the hydrophilic region, the gaseous voids 14 will remain substantially intact during at least a portion of the predetermined time for delivery of an active agent through the mucosal layer by a delivery device incorporating the backing layer. Because molecules do not tend to diffuse through air or other gaseous voids, they are generally forced to diffuse around the voids, causing them to follow a more tortuous path through the backing layer.

The purpose of the disperse non-hydrophilic region is to inhibit migration of a drug or other active agent contained within the active layer through the backing layer during use of the delivery device to deliver a drug or other active agent through a mucosal surface (not shown). It has been found that including a dispersed non-hydrophilic region inhibits migration of molecules by creating a tortuous or circuitous path along which the drug or other active agent must migrate to avoid the intermittent barriers formed by the dispersed non-hydrophilic region. In this way, the dispersed non-hydrophilic region creates an effective diffusion path that is greater than the actual thickness of the backing layer. In addition, the non-hydrophilic region reduces the surface area through which drug or other active agents can diffuse through. In this way, the effective area for diffusion is smaller than the actual surface area of the backing layer.

By way of illustration and not limitation, if the existence of the gaseous voids 14 results in a diffusion path that is twice as long as the thickness of the backing layer, one would expect the time for diffusion of a molecule through the backing layer to approximately double. In this way, a backing layer having a thickness x may provide barrier properties that approximate those of a backing layer having a thickness 2x. Nevertheless, the foregoing relationship is given purely by way of illustration and should not be understood as implying any particular relationship between the thickness of exemplary backing layers according to the invention and/or the concentration of gaseous voids and the time it takes for a particular molecule to diffuse through the backing layer.

In addition to providing a tortuous pathway, the surface area available for diffusion is also reduced due to voids, droplets or particles. For a surface area in which half is occupied by voids, droplets or particles, the flux is reduced by approximately one half; therefore, the barrier properties of the backing layer is essentially doubled.

Figure 2:
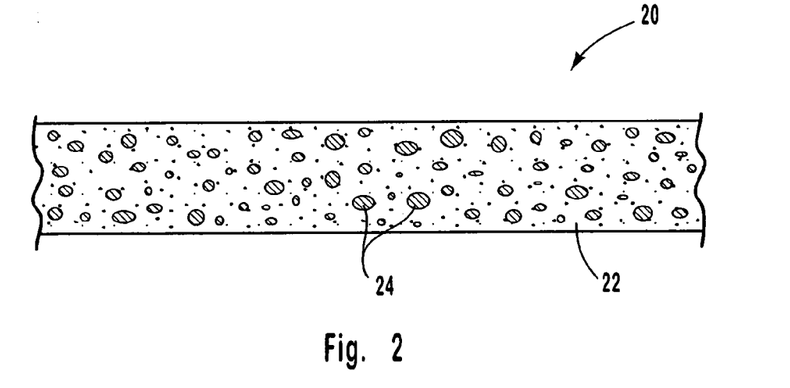
FIG. 2 is a cross-section view illustrating an alternative backing layer according to the invention comprising a continuous hydrophilic region or component and a disperse non-hydrophilic region or component comprising a liquid or solid material.

FIG. 2 illustrates an alternative backing layer 20 according to the invention that includes a continuous hydrophilic region 22 and a disperse non-hydrophilic region 24 comprising a hydrophobic liquid or solid or a solid that is not readily soluble in water. As can be readily imagined, upon dissolving of the hydrophilic region 22, the liquid droplets or solid particles comprising the non-hydrophilic region 24 will readily disperse within a patient's oral cavity or other location.

Figure 3:
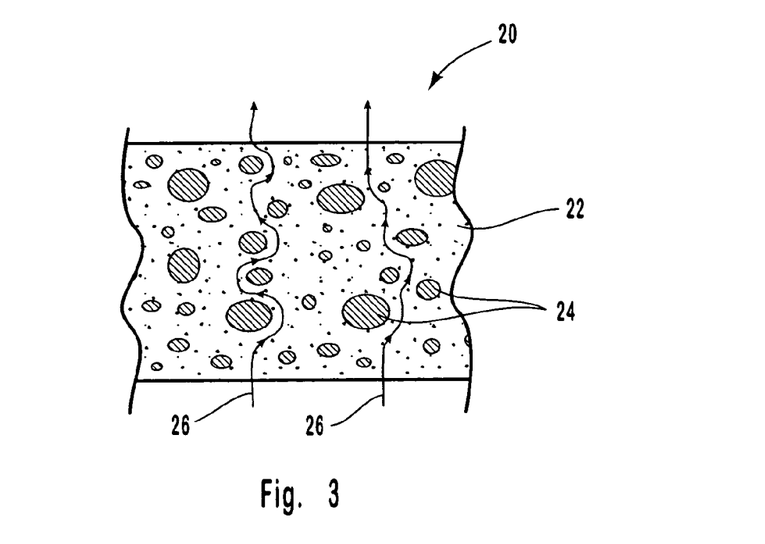
FIG. 3 is a cross-section view of an inventive backing layer illustrating the concept of a tortuous or circuitous route that a drug or other active molecule must take in order to diffuse through the backing layer.

FIG. 3 illustrates hypothetical diffusion paths 26 through an inventive backing layer, such as backing layer 20 comprising a hydrophilic region 22 and a disperse non-hydrophilic region 24 comprising a liquid or solid. As shown in FIG. 3, the diffusion paths 26 deviate from a straight line and therefore necessarily lengthen the diffusion paths that would otherwise exist in the absence of the disperse non-hydrophilic region 24.

Figure 4:
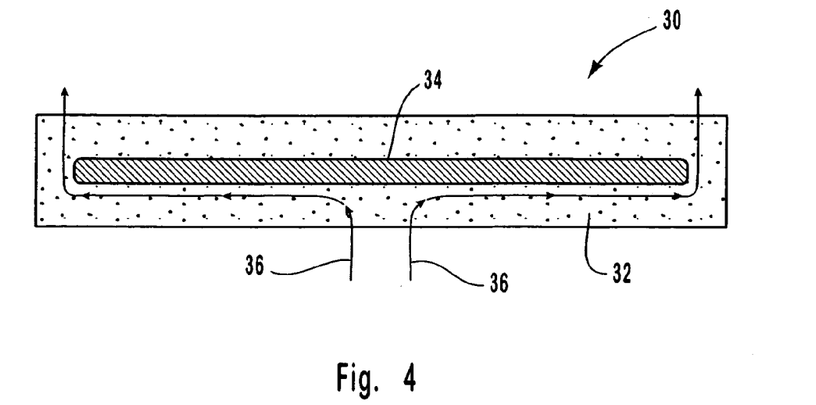
FIG. 4 is a cross-section view illustrating an alternative backing layer according to the invention that includes a continuous hydrophilic region or component surrounding a continuous non-hydrophilic region or component that is entirely encapsulated within the hydrophilic region.

FIG. 4 depicts an alternative backing layer 30 according to the invention that includes a continuous hydrophilic region 32 that completely surrounds or encapsulates a continuous non-hydrophilic region or component 34. The continuous non-hydrophilic region 34 effectively forms a barrier such that any diffusion of drugs or other targeted molecules must follow diffusion path 36 that entirely bypass the continuous non-hydrophilic region 34.

Figure 5:
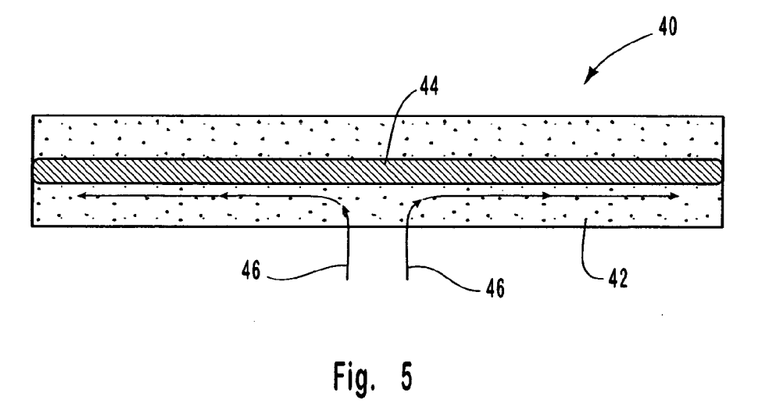
FIG. 5 is a cross-section view illustrating an alternative backing layer comprising two continuous layers of a hydrophilic region separated by a non-hydrophilic region sandwiched therebetween.

FIG. 5 depicts an alternative backing layer 40 that includes a hydrophilic region 42 that is at least partially bifurcated by a non-hydrophilic region 44 sandwiched or layered between two halves of the hydrophilic region 42. It should be understood that because FIG. 5 is merely a cross-section, the non-hydrophilic region 44 may terminate in unseen dimensions short of the hydrophilic region 42 such that the hydrophilic region 42 may comprise a continuous phase. Because the non-hydrophilic region 44 extends to the end of the hydrophilic region 42, it causes the diffusion paths 46 to bypass the non-hydrophilic region 42 and follow diffusion paths out the sides, rather than the top, of the backing layer 40.

Figure 6:
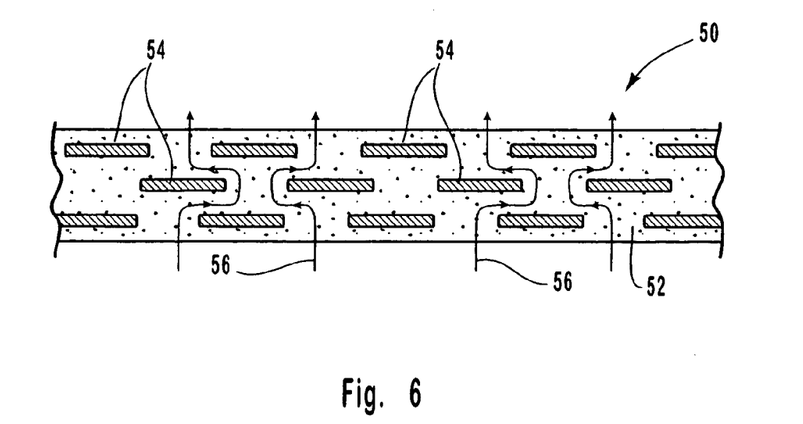
FIG. 6 is a cross-section view illustrating an alternative backing layer comprising a continuous hydrophilic region or component and a plurality of elongated non-hydrophilic regions dispersed within the hydrophilic region.

FIG. 6 illustrates an alternative backing layer 50 according to the invention that includes a continuous hydrophilic region 52 and a plurality of elongated non-hydrophilic regions 54 that overlap in a manner so as to yield a nonlinear diffusion path 56 through the backing layer 50. The non-hydrophilic regions 54 are in one sense a disperse phase. Nevertheless, because they are elongated, they behave in some ways more like the continuous non-hydrophilic regions illustrated in FIGS. 4 and 5. The main purpose of FIG. 6 is to illustrate that there are a wide range of possible non-hydrophilic regions between the highly disperse phases depicted in FIGS. 1 and 2 and the continuous phases depicted in FIGS. 4 and 5.

Figure 7:
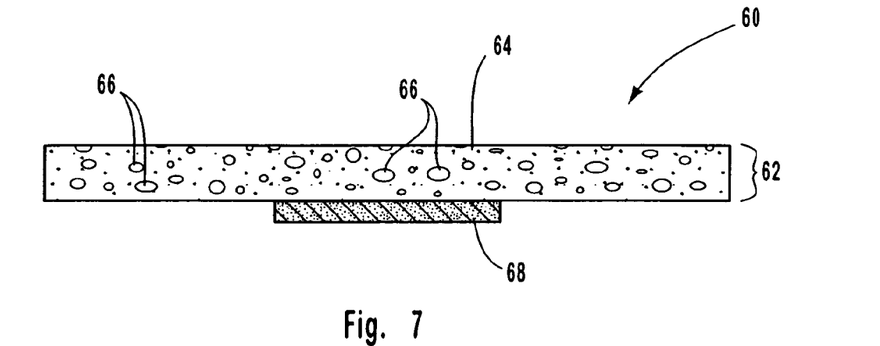
FIG. 7 is a cross-sectional view illustrating a transmucosal device comprising a backing layer according to the invention and an active layer comprising a drug or other active agent adjacent to the backing layer.

FIG. 7 depicts delivery device 60 comprising a backing layer 62 according to the invention that includes a hydrophilic region 64 and a disperse non-hydrophilic region 66. Adjacent to the backing layer 62 is an active layer 68 comprising a drug or other active agent for delivery into a patient or animal. In a preferred embodiment, the backing layer 62 will resist dissolving when exposed to saliva or other sources of moisture during a prescribed period of time in order for the delivery device 60 to isolate and maintain the active layer 68 against the delivery site for a time sufficient for a drug or other active agent therein to be delivered as desired and not diffused into the oral cavity or other location away from the targeted delivery site.

Figure 8:
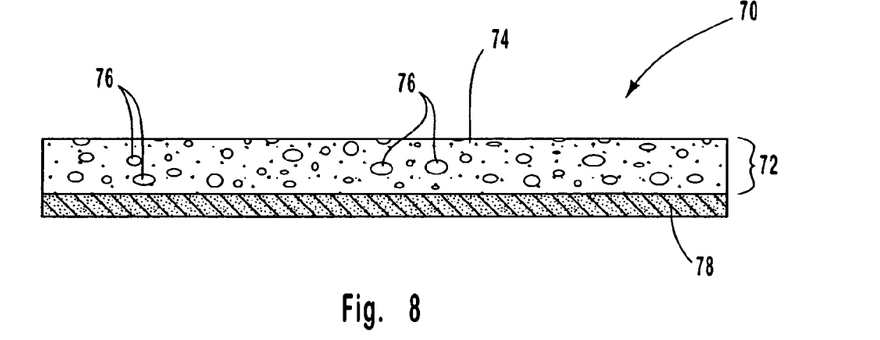
FIG. 8 is a cross-section view illustrating a delivery device comprising a backing layer according to the invention adjacent to an active layer that extends along an entire length of the backing layer.

FIG. 8 depicts an alternative delivery device 70 comprising an inventive backing layer 72 having a hydrophilic region 74 and a dispersed non-hydrophilic region 76. An active layer 78 comprising a drug or other active agent is depicted as extending along an entire length of the backing layer 72.

Figure 9:
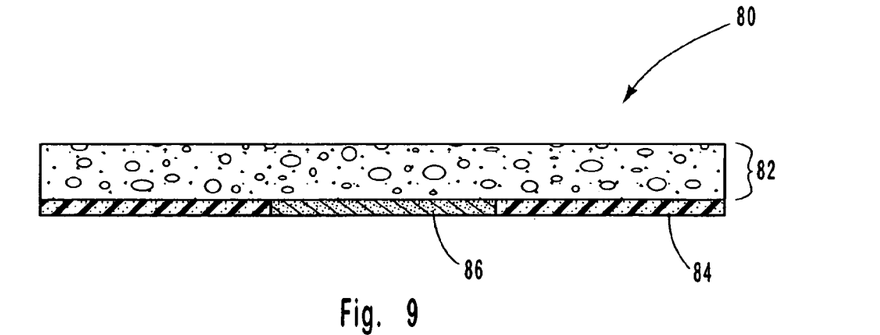
FIG. 9 is a cross-section view illustrating a delivery device comprising a backing layer according to the invention, an active layer adjacent to the backing layer, and an adhesive layer adjacent to the backing layer and circumscribing the active layer.

FIG. 9 depicts an alternative delivery device 80 comprising an inventive backing layer 82 according to the invention, an adhesive layer 84 adjacent to a portion of the backing layer and an active layer 86 adjacent to a portion of the backing layer, with the adhesive layer 84 circumscribing at least a portion of the active layer 86. In this way, the adhesive layer can assist the backing layer in isolating and maintaining the drug or other active ingredient in the active layer 86 within a targeted delivery region.

Figure 10:
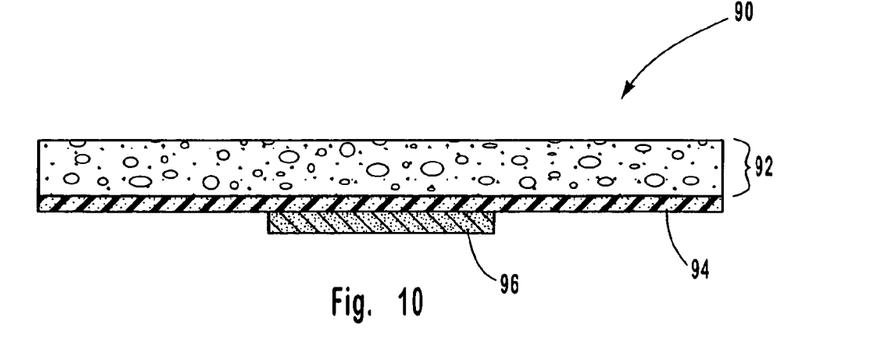
FIG. 10 is a cross-section view illustrating a delivery device comprising a backing layer according to the invention, an adhesive layer adjacent to the backing layer, and an active layer adjacent to the adhesive layer and sized so that a portion of the adhesive layer circumscribes or extends beyond the active layer.

FIG. 10 depicts an alternative delivery device 90 comprising an exemplary backing layer 92 according to the invention, an adhesive layer 94 adjacent to and extending along an entire length of the backing layer 92 and an active layer 96 adjacent to a portion of the adhesive layer 94. In this embodiment, the adhesive layer 94 also circumscribes at least a portion of the active layer 96, at least within the cross-section depicted in FIG. 10.

It should be understood that the delivery device as depicted in FIGS. 1-10 are merely illustrative. The relative lengths, widths and thicknesses of the various layers (e.g., backing layer, adhesive layer and active layer) can be adjusted as desired to yield a delivery device having the desired properties.

The inventive backing layers according to the invention can be used in the manufacture of transmucosal delivery devices having any desired drug or other active agent. The drug or other active agent will typically comprise a discrete active layer or region adjacent to the inventive backing layers according to the invention. Although, it is contemplated that the inventive backing layer contains no drug or active agent initially when the transmucosal delivery devices are manufactured, it is within the scope of the invention for the active layer or region, some time after the transmucosal delivery devices are manufactured, to be at least partially dispersed within the inventive backing layer. In a preferred embodiment the active layer or region of the transmucosal delivery devices according to the invention include a drug or other active agent and at least one enhancer.

Examples of drugs or other active agents that may be used in transmucosal delivery devices according to the invention include fentanyl, codeine, sufentanil, lofentanil, carfentanil, alfentunil, morphine, other opiates, sumatriptan, other triptans, interferons, heparin, proteins, peptides, and barbiturates, analgesics, anesthetics, anxolytics, sedatives, antidepressants, cannobinoids, anticoagulants, anti-biotics, antihistamines, blood pressure modulators, anti-cholesterol drugs, vitamins, nutrients, etc. Preferred examples of drugs or other active agents that may be used in transmucosal delivery devices according to the invention include fentanyl, codeine, sufentanil, lofentanil, carfentanil, alfentunil, morphine, other opiates, triptans, in particular sumatriptan, interferons, proteins, and peptides. Preferred examples of drugs or other active agents that may be used in transmucosal delivery devices according to the invention include triptans, in particular sumatriptan, interferons, proteins, peptides, and any drug that requires an enhancer to promote diffusion of the drug or active agent in transmucosal delivery.

Examples of enhancers that may be used to facilitate or accelerate delivery of a drug or other active agent through the mucosal layer, particularly high molecular weight molecules that may otherwise resist diffusion through the mucous membrane, include, but are not limited to, bile acid, their salt forms and derivatives, acyl carnitines, sodium dodecylsulfate, dimethylsulfoxide, sodium laurylsulfate, salts and other derivatives of saturated and unsaturated fatty acids, surfactants, alcohols, terpenes, cyclodextrins and their derivatives, saponins and their derivatives, chitosan, and chelators (e.g., EDTA, citric acid and salicylates). Examples of bile acids, their salt forms and derivatives, include, but are not limited to, sodium cholate, dehydrocholate, sodium glycocholate, sodium glycodeoxycholate, sodium deoxycholate, sodium lithocholate chenocholate, chenodeoxycholate, glycochenocholate, sodium taurocholate, taurodeoxycholate, taurochenocholate, taurochenodeoxycholate, ursocholate, ursodeoxycholate, and hyodeoxycholate, and the like.

Examples of suitable matrix materials that may optionally be included in addition to the drug and enhancer include, but are not limited to, alginic acid, its salts and derivatives, celluloses, cellulose ethers, their salts and derivatives, starches, carrageenan, polyethylene glycol, polyethylene oxide, polyvinyl alcohol, polyvinyl pyrrolidone, acacia, and polyacrylic acids.

In one embodiment, the backing layer according to the invention may be used together with an active layer to form a two-layer transmucosal delivery device or dosage form. In another embodiment, the delivery device may include an adhesive layer adjacent to the backing layer that circumscribes the active layer in order to enhance adhesion between the backing layer and a mucosal surface or membrane to which it is attached during use (e.g., FIGS. 9 and 10).

Transmucosal delivery devices according to the invention may be placed against a mucosal surface or membrane of a mammal in order to deliver one or more active agents across the mucosa (e.g., within an oral cavity, vagina, or intestine). A typical method for delivering an active agent across mucosa comprises (1) placing the transmucosal delivery against a mucosal surface and (2) allowing the transmucosal delivery device to remain against the mucosal surface so as to provide a desired treatment. In a preferred method of treatment, the transmucosal delivery is placed against a mucosal surface within an oral cavity of a mammal. The transmucosal delivery is typically allowed to (3) remain within the oral cavity or against other mucosa until it dissolves.

The transmucosal delivery device may be used to deliver any active agent so as to provide any desired treatment. Such devices are particularly useful for delivering sumatriptan. They may also be used, for example, to deliver opiates or other analgesics to treat pain, including what is known as "breakthrough pain", which refers to pain that is felt by a patient who is already medicated for pain.

EXAMPLES OF EMBODIMENTS

The following examples are given by way of illustration and not limitation. Examples expressed in the past tense define actual compositions of backing layers that have been manufactured. Examples expressed in the present tense are merely hypothetical or prophetic in nature but are based on, or extrapolated from, actual compositions that have been made.

Example 1

A dissolvable backing layer was manufactured by dissolving 20 parts gelatin and 10 parts glycerin in 70 parts water. The mixture was heated to 50° C. to dissolve the gelatin. Once the mixture was fully dissolved, air bubbles were introduced into the gel by means of a high-speed homogenizer at 9,000±1000 rpm. After a few minutes of mixing, the gel changed from being clear to opaque. Gel samples were taken to determine the percentage of air voids within the gel. The homogenization process was stopped once the air voids comprised 50%±5% (v/v) of the gel/air mixture as a disperse non-hydrophilic region. The whipped gel was then cast on a plastic release liner to form a cast backing layer having a thickness of 2 mm. The backing layer was dried overnight at room temperature, yielding final backing layer having a thickness of about 0.7 mm as a result of water evaporation.

Example 2

A dissolvable backing layer was manufactured from 20 parts gelatin, 10 parts glycerin, 1 part sodium alginate and 69 parts water, which together formed a hydrophilic region, and gaseous voids dispersed throughout the hydrophilic region as a disperse non-hydrophilic region. The forming procedure was the same as in Example 1 and yielded a gel/air mixture and subsequent cast backing layer having approximately the same concentration of air voids. The addition of sodium alginate within the formulation yielded a backing layer that was stronger and that lasted longer, relative to Example 1.

Example 3

A dissolvable backing layer was manufactured from 20 parts gelatin, 10 parts glycerin, and 70 parts water, which together formed a hydrophilic region, and 20% by weight of the hydrophilic region of powdered talc (magnesium silicate) dispersed throughout the hydrophilic region as a disperse non-hydrophilic region. The procedures for making the hydrophilic region and backing layer were the same as in the Example 1.

Example 4

A dissolvable backing layer was manufactured from 20 parts gelatin, 10 parts glycerin, and 70 parts water, which together formed a hydrophilic region, and 5% by weight of the hydrophilic region of Crisco® oil (a partially hydrogenated vegetable oil) dispersed throughout the hydrophilic region as a disperse non-hydrophilic region. The procedures for making the hydrophilic region and backing layer were the same as in the Example 1.

Example 5

A dissolvable backing layer was manufactured from 20 parts gelatin, 10 parts glycerin, and 70 parts water, which together formed a hydrophilic region, and 10% by weight of the hydrophilic region of Lubritab® (a hydrogenated vegetable oil) dispersed throughout the hydrophilic region as a disperse non-hydrophilic region. The mixture was heated to 70° C. in order to dissolve the gelatin within a hydrophilic region and to cause the hydrogenated vegetable oil to become a liquid as a hydrophobic phase. A high-speed homogenizer was used to whip the two phases together so that the mixture formed an oil-in-water emulsion. The temperature was then lowered to around 40° C. while the homonegizer was running. At this temperature, the hydrogenated vegetable oil solidified while the gelatin gel remained liquid. The mixture thus became a solid-in-liquid suspension. Upon casting the mixture on a plastic release liner, the gelatin gel solidified and the solid hydrogenated vegetable oil particles remained permanently dispersed as a non-hydrophilic region within the continuous hydrophilic gelatin matrix. The thickness of the cast backing layer was 1.5 mm. The backing layer was dried overnight at room temperature, yielding final backing layer having a thickness of about 0.35 mm as a result of water evaporation.

Example 6

A dissolvable backing layer was manufactured from 20 parts gelatin, 10 parts glycerin, and 70 parts water, which together formed a hydrophilic region, and 5% by weight of the hydrophilic region of magnesium stearate dispersed throughout the hydrophilic region as a disperse non-hydrophilic region. The procedures of making the hydrophilic region and casting the backing layer were the same as in the Example 1.

Example 7

A dissolvable backing layer was manufactured from 20 parts gelatin, 10 parts glycerin, 0.5 part agarose, and 69.5 parts water, which together formed a hydrophilic region, and gaseous voids dispersed throughout the hydrophilic region as a disperse non-hydrophilic region. The manufacturing procedures were the same as in the Example 1. The addition of agarose yielded a backing layer that was stronger and that lasted longer, relative to Example 1.

Example 8

A dissolvable backing layer was manufactured from 20 parts gelatin, 10 parts glycerin, 0.53 part peppermint oil, 2.19 parts acesulfame potassium, and 67.28 parts water, which together formed a flavored hydrophilic region, and gaseous voids dispersed throughout the hydrophilic region as a disperse non-hydrophilic region. The manufacturing procedures were the same as in the Example 1. The addition of a flavorant and sweetener yielded a backing layer that tasted better. This would be expected to improve patient compliance.

Example 9

A dissolvable backing layer was manufactured from 20 parts gelatin, 10 parts glycerin, 0.1 part sodium lauryl sulfate, and 69.9 parts water, which together formed a hydrophilic region, and gaseous voids dispersed throughout the hydrophilic region as a disperse non-hydrophilic region. The manufacturing procedures were the same as in the Example 1. The surfactant (sodium lauryl sulfate) was used to stabilize the gaseous voids in the hydrophilic region.

Comparative Example 1

A group of backing layers for comparative testing were manufactured using the formulations and procedures stated in Example 1 (aerated), Example 3 (talc), Example 5 (hydrogenated vegetable oil), and Example 6 (Mg stearate). A clear backing layer (clear) was manufactured for purposes of comparison according to Example 1 but without a non-hydrophilic region, i.e., the backing layer had the same hydrophilic region as the aerated backing layer but without any non-hydrophilic region dispersed therein. Diffusion studies were conducted to test the barrier function of the various backings discussed above using side-by-side diffusion chambers.

Figure 11:
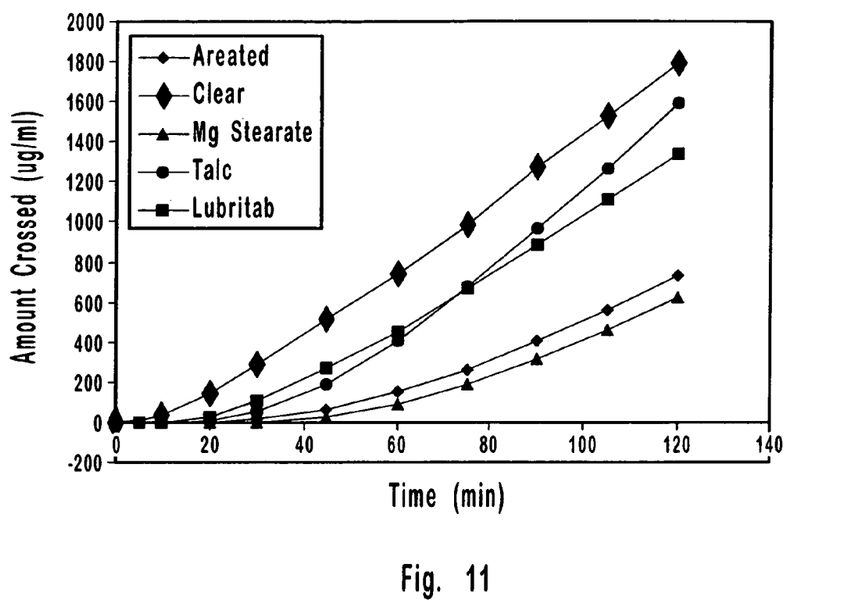
FIG. 11 is chart depicting the results of a diffusion study that compared the diffusion rates of sumatriptan across various backing layers manufactured according to the invention, as well as a clear backing layer as a baseline comparison.

FIG. 11 is a chart that graphically depicts the amount of sumatriptan that crossed the membrane over time for each of the backing layers, as was determined using HPLC. As is readily shown, the diffusion of sumatriptan across the backing layer was greatest for the "clear" backing layer that did not include a non-hydrophilic region. The backing layers that included a non-hydrophilic region all demonstrated significantly reduced diffusion of sumatriptan across the backing layer, particularly during the early stages of the test. Additonal data (not shown) indicate that the addition of a non-hydrophilic region not only increased the barrier function of the backing layer, but also slowed down the hydration rate of the hydrophilic regions comprising the gelatin gel, thus further increasing the barrier function of the backing layer during its hydration period.

Comparative Example 2

To further illustrate the actual use of the inventive backing layers as a protective layer for a transmucosal patch, three types of backing materials were made according to Example 1 (aerated), Example 4 (partially hydrogenated vegetable oil), and Example 6 (Mg stearate). In this study, the active formulation comprised 10 mg sumatriptan, 5 mg sodium taurocholic acid, and sodium alginate. The active layers were 0.75 inches in diameter. The backing layers were 0.875 inches in diameter. The active and backing layers were "glued" together by moistening them with water prior to the in vivo experiments.

In vivo experiments were conducted on the oral mucosa of anesthetized dogs over a period of two hours. The oral mucosa were washed and wetted with saline before application of the patch. During the experiments, Telfa® pads (surgical dressing, Kendall Co.), soaked with warm saline, were placed on top of the patch to simulate actual environment in the oral cavity. The pads were replaced every 5 minutes until the patch dissolved. The idea was to simulate normal wear and tear of the patch in the oral cavity. Serum samples were taken at predetermined intervals. Samples were analyzed using HPLC with an MS detector.

Figure 12:
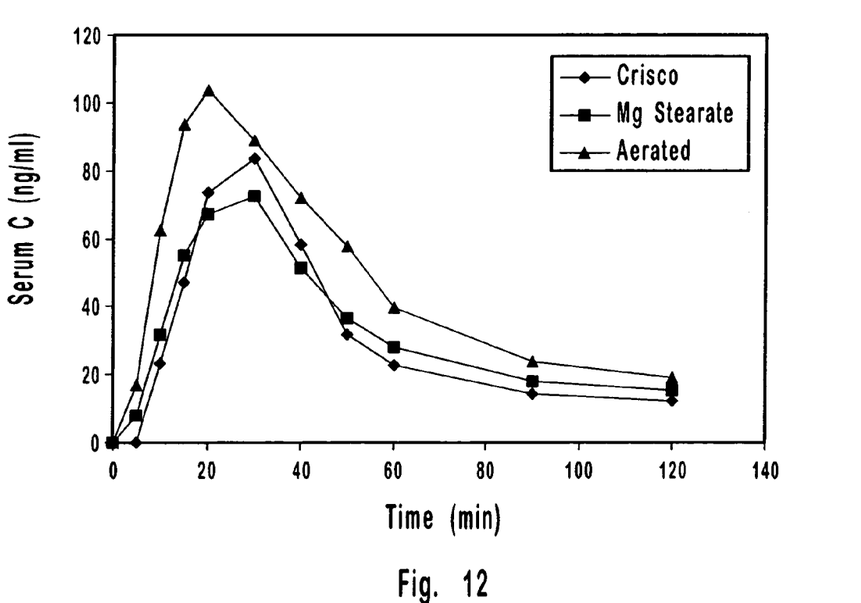
FIG. 12 is chart depicting the results of an in vivo study that measured serum sumitriptan concentrations as a function of time using different backing layers according to the invention.

The data from this study are tabulated in the chart depicted in FIG. 12. They show that the backing layers offered adequate protection during the first 30 to 40 minutes to cause rapid uptake by the dogs of sumatriptan. Upon dissolution of the backing and active patches, the serum concentration started to decline. The serum data closely coincided with patch administration, in which the patches lasted 30 to 50 minutes in the oral cavity.

Example 10

A transmucosal drug delivery device was manufactured having a dissolvable backing layer, an adhesive layer, and an active layer. The dissolvable backing layer was manufactured from a gel that comprised 20% gelatin and 10% glycerin, with the balance being water, which together formed a hydrophilic region, and gaseous voids dispersed throughout the hydrophilic region as a dispersed non-hydrophilic region. The hydrophilic region comprised 50% by volume of the backing layer while the voids comprised 50% by volume. The backing layer was cast on a plastic substrate. The thickness of the backing layer was 2 mm when first cast. The backing layer was allowed to solidify without drying.

The adhesive layer was formed from an aqueous gel that comprised 2.5% Polyox® 750 (a polyethylene oxide), 0.5% Carbopol® 971 (a polyacrylic acid), with the balance being water. The gel was cast directly onto the solidified backing layer to form the adhesive layer, which had a thickness of 1 mm when first cast. The combined backing and adhesive layers were dried overnight at room temperature. The active layer was formed from an aqueous mixture that comprised 6% sodium alginate, 4% sumatriptan as a succinate salt, 2% sodium taurocholic acid, with the balance being water. The mixture was cast directly onto the exposed surface of the dried adhesive layer to form the active layer having of 1 mm when first cast. The dosage form was then dried overnight at room temperature.

Example 11

An oral transmucosal delivery patch containing an interferon as the active agent was made according to the current invention. The patch had three layers: (1) an active layer, (2) an adhesive layer, and (3) a backing layer. The formulations of the three layers are listed in the following tables.

| Ingredient Name | Concentration (%) |
|---|---|
| Active Layer Ingredients | |
| Sodium Alginate | 2% |
| Interferon α2b | 0.1% |
| Sodium Taurocholate | 0.8% |
| Water | 97.1% |
| Adhesive Layer Ingredients | |
| Polyethylene oxide | 2.5% |
| Polyacrylic acid | 0.5% |
| Water | 97.5% |
| Backing Layer Ingredients | |
| Gelatin | 20% |
| Glycerin | 10% |
| Dodecyltrimethylammonium Bromide | 0.1% |
| Water | 70% |

A gel composition used to form the active layer was prepared by mixing the sodium alginate, interferon α2b, and sodium taurocholate as dry ingredients in a mixing can. Then an appropriate amount of water was added. The mixing can was rolled slowly on a roller mixer to avoid trapping excessive air inside the gel. Once the gel was adequately mixed (i.e., free of solid alginate particles), it was pipetted onto a plurality of 0.875 inch polystyrene disks at 1 ml per disk to form an active layer. The gel was dried at room temperature overnight to form the finished active layer. A gel composition used to form the backing layer was prepared by mixing the gelatin, glycerin and dodecyltrimethylammonium bromide in 55° C. water. Once the gelatin was fully dissolved, an overhead mixer was used to whip the gel at 1500 rpm until the gel turned white and the volume doubled so as to form a foamed gel composition. The foamed gel composition was then cast in a plastic mold having a diameter of 1 inch and a thickness of 0.125 inch. The cast gel composition was allowed to dry at room temperature overnight to form the finished backing layer.

A gel composition used to form the adhesive layer was prepared by roll-mixing the ingredients in a mixing can. A thin layer, about 1 mm in thickness, was applied to the exposed surface of the dried backing layer. The combined backing and adhesive layers were dried together overnight at room temperature.

Once the backing, adhesive and active layers were ready, 25 μl of water was pipetted onto an exposed surface of the adhesive layer, and the active layer was peeled from the polystyrene disk and placed onto the moistened adhesive layer surface. The active layer was pressed gently until it sat flat on top of the adhesive/backing layer. The combined patch was then allowed to dry at room temperature.

Example 12

An oral transmucosal delivery patch containing sumatriptan as the active agent was made according to the current invention. The patch had three layers: (1) an active layer, (2) an adhesive layer, and (3) a backing layer. The formulations of the three layers are listed in the following tables.

| Ingredient Name | Concentration (%) |
| --- | --- |
| Active Layer Ingredients | |
| Sodium Alginate | 4% |
| Sumatriptan Succinate | 11.2% |
| Sodium Taurocholate | 4% |
| Water | 80.8% |
| Adhesive Layer Ingredients | |
| Polyethylene oxide | 2.5% |
| Polyacrylic acid | 0.5% |
| Water | 97.5% |
| Backing Layer Ingredients | |
| Gelatin | 20% |
| Glycerin | 10% |
| Sodium Alginate | 0.25% |
| Acesulfame Potassium | 0.075% |
| Water | 69.675% |

A gel composition used to form the backing layer was made by dissolving the gelatin in 50° C. water containing the glycerin and sodium alginate. The gel was put in an oven heated to 50° C. to cause the gelatin to dissolve completely. Once the gelatin was thoroughly dissolved, the acesulfame potassium was added as sweetener. The gel composition was aerated by a high shear homogenizer to yield a foamed gel composition. The gel composition was cast on a plastic release liner to form an unsolidified sheet having a thickness of 2.2 mm using a casting block. The sheet was allowed to solidify without drying.

A gel composition used to form the adhesive layer was made by dissolving the non-water ingredients in the water. The adhesive gel composition was mixed under vacuum for about 6 hours until the gel became clear without lumps. The adhesive gel composition was cast on the solidified backing layer formed in the immediately preceding paragraph. The setting for the casting block was maintained at 2.2 mm. Since the backing layer shrank to about 1.2 mm upon solidifying, the actual thickness of the adhesive layer was about 1 mm. The combined backing/adhesive layers were allowed to dry at room temperature overnight.

A gel composition used to form the active layer was made by dry mixing the non-water ingredients in a mixing container and then roll-mixing the gel on a roller for 6 hours after addition of the water. The active gel composition was sonicated for a few minutes to eliminate air bubbles. A plastic mold having a plurality of mold cavities with a diameter of 0.6875 inch and a thickness of 0.5 mm was placed over a portion of the backing/adhesive layer. The active gel composition was cast inside the plastic mold cavities and the excess gel composition was cut using a stainless steel blade. The plastic mold was then removed. Once the active layer was dried, tri-layer patches were cut out using a 0.8125 inch diameter die cutter. The finished products were tri-layer patches in which the active layers were smaller than (i.e., circumscribed by) the backing/adhesive layers.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dissolvable backing layer for use with a transmucosal delivery device adapted for placement against mucosa, comprising:
    a hydrophilic region comprising at least one hydrophilic polymer that is adapted to dissolve over time when exposed to moisture; and
    a non-hydrophilic region at least partially encapsulated within said hydrophilic region and that is adapted to at least partially inhibit migration of water, active agents or other molecules through the backing layer and that is adapted to disperse when no longer encapsulated within said hydrophilic region.

2. The dissolvable backing layer of claim 1, said hydrophilic polymer comprising at least one component selected from the group consisting of gelatin, other proteins, pectin, agar, chitosan, carrageenan, starch, modified starch, cellulose ethers, cellulose esters, other cellulose derivatives, polyvinyl alcohol, polyvinyl pyrrolidone, cross-linked povidone, guar gum, poloxamer, polyethylene glycol, polyethylene oxide, polyacrylic acid, sodium alginate, xanthan gum, and derivatives thereof.

3. The dissolvable backing layer of claim 1, said hydrophilic polymer having a concentration in a range of about 1% to 100% by weight of said hydrophilic region.

4. The dissolvable backing layer of in claim 1, said hydrophilic polymer having a concentration in a range of about 5% to about 90% by weight of said hydrophilic region.

5. The dissolvable backing layer of claim 1, said hydrophilic polymer having a concentration in a range of about 10% to about 80% by weight of said hydrophilic region.

6. The dissolvable backing layer of claim 1, said hydrophilic region further comprising at least one plasticizer.

7. The dissolvable backing layer of claim 6, said plasticizer comprising at least one component selected from the group consisting of glycerin, propylene glycol, polyethylene glycol, polypropylene glycol, sugar alcohols, and corn syrup.

8. The dissolvable backing layer of claim 6, said plasticizer having a concentration in a range of 0% to about 80% by weight of said hydrophilic region.

9. The dissolvable backing layer of claim 6, said plasticizer having a concentration in a range of about 2% to about 60% by weight of said hydrophilic region.

10. The dissolvable backing layer of claim 6, said plasticizer having a concentration in a range of about 5% to about 50% by weight of said hydrophilic region.

11. The dissolvable backing layer of claim 1, said hydrophilic region comprising a continuous phase and said non-hydrophilic region comprising a disperse phase.

12. The dissolvable backing layer of claim 11, said non-hydrophilic region comprising a plurality of gaseous voids dispersed throughout said hydrophilic region.

13. The dissolvable backing layer of claim 11, said non-hydrophilic region comprising a plurality of hydrophobic liquid droplets or hydrophobic solid particles dispersed throughout said hydrophilic region.

14. The dissolvable backing layer of claim 13, said hydrophobic liquid droplets or hydrophobic solid particles comprising at least one component selected from the group consisting of oils, vegetable oils, mineral oils, silicone liquids, waxes, magnesium stearate, fats, fatty acids, salts of fatty acids, waxes, polymers, polymeric beads, and solid silicone particles.

15. The dissolvable backing layer of claim 1, said non-hydrophilic region comprising a plurality of water-insoluble inorganic filler particles dispersed throughout said hydrophilic region.

16. The dissolvable backing layer of claim 15, said water-insoluble inorganic filler particles comprising at least one component selected from the group consisting of talc, sand, silica, alumina, titanium dioxide, other transition metal oxides, silicates, limestone, and ground geologic materials.

17. The dissolvable backing layer of claim 1, said hydrophilic and non-hydrophilic regions each comprising a continuous phase.

18. The dissolvable backing layer of claim 17, said non-hydrophilic region comprising at least one of a hydrophobic liquid, hydrophobic solid, or non-water soluble solid.

19. The dissolvable backing layer of claim 17, said non-hydrophilic region comprising at least one component selected from the group consisting of oils, vegetable oils, mineral oils, waxes, magnesium stearate, fats, fatty acids, salts of fatty acids, waxes, polymeric beads, polymers and silicones.

20. The dissolvable backing layer of claim 17, said non-hydrophilic region comprising at least one initially solid component that transforms into a liquid or softened solid when warmed to body temperature.

21. The dissolvable backing layer of claim 1, said non-hydrophilic region comprising at least two different types of components selected from the group consisting of gaseous voids, hydrophobic liquids, hydrophobic solids, and water-insoluble inorganic filler particles.

22. The dissolvable backing layer of claim 1, said hydrophilic region comprising about 10% to about 95% by volume of the backing layer and said non-hydrophilic region comprising about 5% to about 90% by volume of the backing layer.

23. The dissolvable backing layer of claim 1, said hydrophilic region comprising about 15% to about 90% by volume of the backing layer and said non-hydrophobic region comprising about 10% to about 85% by volume of the backing layer.

24. The dissolvable backing layer of claim 1, said hydrophilic region comprising about 20% to about 85% by volume of the backing layer and said non-hydrophobic region comprising about 15% to about 80% by volume of the backing layer.

25. The dissolvable backing layer of claim 1 the backing layer having a thickness in a range of about 0.1 mm to about 5 mm.

26. The dissolvable backing layer of claim 1, the backing layer having a thickness in a range of about 0.2 mm to about 3.5 mm.

27. The dissolvable backing layer of claim 1, the backing layer having a thickness in a range of about 0.3 mm to about 2 mm.

28. The dissolvable backing layer of claim 1, the backing layer having a formulation and thickness in order for the backing layer to become dissolved within the oral cavity when exposed to saliva within a prescribed time period or range.

29. The dissolvable backing layer of claim 1, the backing layer having a formulation and thickness in order for the backing layer to become dissolved within the oral cavity when exposed to saliva within a time period in a range of about 1 minute to about 2 hours.

30. The dissolvable backing layer of claim 1, the backing layer having a formulation and thickness in order for the backing layer to become dissolved within the oral cavity when exposed to saliva within a time period in a range from about 10 minutes to about 1 hour.

31. The dissolvable backing layer of claim 1, the backing layer decreasing the permeability coefficient of one or more water soluble molecules by at least about 25% compared to a backing layer in the absence of the non-hydrophilic region.

32. The dissolvable backing layer of claim 1, the backing layer decreasing the permeability coefficient of one or more water soluble molecules by at least about 50% compared to a backing layer in the absence of the non-hydrophilic region.

33. The dissolvable backing layer of claim 1, the backing layer decreasing the permeability coefficient of one or more water soluble molecules by at least about 75% compared to a backing layer in the absence of the non-hydrophilic region.

34. A dissolvable backing layer of claim 1 comprising:
a hydrophilic region comprising at least one hydrophilic polymer having a concentration in a range of about 10% to about 80% by weight of said hydrophilic region and at least one plasticizer having a concentration in a range of about 5% to about 50% by weight of said hydrophilic region, said hydrophilic region is adapted to dissolve over time when exposed to moisture; and
a non-hydrophilic region at least partially encapsulated within said hydrophilic region comprising at least one of gaseous voids, a hydrophobic liquid, a hydrophobic solid, or a non-water soluble solid, and that is adapted to at least partially inhibit migration of water, active agents or other molecules through the backing layer and that is adapted to disperse when no longer encapsulated within said hydrophilic region;
said backing layer having a thickness in a range of about 0.1 mm to about 5 mm.

35. A dissolvable backing layer of claim 1 comprising:
a hydrophilic region comprising gelatin and glycerin that is adapted to dissolve over time when exposed to moisture; and
a non-hydrophilic region at least partially encapsulated within said hydrophilic region comprising at least one of gaseous voids, a hydrophobic liquid, a hydrophobic solid, or a non-water soluble solid, and that is adapted to at least partially inhibit migration of water, active agents or other molecules through the backing layer and that is adapted to disperse when no longer encapsulated within said hydrophilic region;
said backing layer having a thickness in a range of about 0.1 mm to about 5 mm.

36. A dissolvable backing layer for use with a transmucosal delivery device adapted for placement against mucosa, comprising:
a hydrophilic region comprising gelatin and glycerin and that is adapted to dissolve over time when exposed to saliva; and
gaseous voids comprising a disperse phase encapsulated within said hydrophilic region in a manner so as to at least partially inhibit migration of water, active agents or other molecules through said backing layer,
said backing layer comprising a sheet or film having a thickness in a range of about 0.1 mm to about 5 mm.

37. The dissolvable backing layer of claim 36, said hydrophilic region comprising about 20% to about 85% by volume of the backing layer and said gaseous voids comprising about 15% to about 80% by volume of the backing layer.

38. The dissolvable backing layer of claim 36, the backing layer comprising a sheet or film having a thickness in a range of about 0.2 mm to about 3.5 mm.

39. The dissolvable backing layer of claim 36, the backing layer comprising a sheet or film having a thickness in a range of about 0.3 mm to about 2 mm.

40. The dissolvable backing layer as defined in claim 36, the backing layer becoming dissolved within the oral cavity when exposed to saliva within a time period and a range of about 1 minute to about 2 hours.

41. The dissolvable backing layer as defined in claim 36, the backing layer becoming dissolved within the oral cavity when exposed to saliva within a time period and a range of about 10 minutes to about 1 hour.

42. A dosage form adapted for transmucosal delivery of an active agent comprising:
an active layer comprising at least one active agent; and
a dissolvable backing layer sized and configured so as to cover a side of said active region, said backing layer comprising:
a hydrophilic region comprising at least one hydrophilic polymer that is adapted to dissolve over time when exposed to moisture; and
a non-hydrophilic region at least partially encapsulated within said hydrophilic region that is adapted to at least partially inhibit migration of said active agent through said backing layer and that is adapted to disperse when no longer encapsulated within said hydrophilic region.

43. The dosage form of claim 42, said active agent comprising at least one drug.

44. The dosage form of claim 42, said active agent comprising sumatriptan.

45. The dosage form of claim 42, said active agent comprising at least one natural or synthetic opiate.

46. The dosage form of claim 42, said active agent comprising at least one of a vitamin or nutrient.

47. The dosage form of claim 42, said active agent comprising at least one member selected from the group consisting of fentanyl, codeine, sufentanil, lofentanil, carfentanil, alfentunil, morphine, other opiates, triptans, interferons, heparin, proteins, peptides, and barbiturates, analgesics, anesthetics, anxolytics, sedatives, anti-depressants, cannobinoids, anticoagulants, antibiotics, antihistamines, blood pressure modulators, and anti-cholesterol drugs.

48. The dosage form of claim 42, said backing layer being sized and positioned relative to the active layer so that the backing layer extends beyond and circumscribes said active layer.

49. The dosage form of claim 42, the dosage form being adapted for use in an oral cavity of a mammal.

50. The dosage form of claim 42, the dosage form comprising at least one other layer in addition to said active layer and said backing layer.

51. The dosage form of claim 50, said other layer being interposed at least partially between said active layer and said backing layer.

52. A method for delivering an active agent across mucosa, comprising:
placing a transmucosal delivery against a mucosal surface, said transmucosal delivery device comprising:
an active layer comprising at least one active agent; and
a dissolvable backing layer sized and configured so as to cover a side of said active region, said backing layer comprising:
a hydrophilic region comprising at least one hydrophilic polymer that is adapted to dissolve over time when exposed to saliva; and
a non-hydrophilic region at least partially encapsulated within said hydrophilic region that is adapted to at least partially inhibit migration of said active agent through said backing layer and that is adapted to disperse when no longer encapsulated within said hydrophilic region; and
allowing said transmucosal delivery device to remain against said mucosal surface so as to provide a desired treatment.

53. The method of claim 52, said transmucosal delivery device being placed into an oral cavity of a mammal.

54. The method of claim 53, said transmucosal delivery device being allowed to remain within the oral cavity until it dissolves.

55. The method of claim 52, said active agent comprising at least one drug.

56. The method of claim 52, said active agent comprising sumatriptan.

57. The method of claim 52, said active agent comprising at least one natural or synthetic opiate.

58. The method of claim 57, said transmucosal delivery device being used to treat breakthrough pain.

59. The method of claim 52, said active agent comprising at least one member selected from the group consisting of fentanyl, codeine, sufentanil, lofentanil, carfentanil, alfentunil, morphine, other opiates, triptans, interferons, heparin, proteins, peptides, and barbiturates, analgesics, anesthetics, anxolytics, sedatives, anti-depressants, cannobinoids, anti-coagulants, anti-biotics, antihistamines, blood pressure modulators, and anti-cholesterol drugs.

60. The method of claim 52, said transmucosal delivery device further comprising at least one additional layer interposed at least partially between said active layer and said backing layer.

* * * * *